(12) United States Patent
Gonzalez et al.

(10) Patent No.: US 8,092,685 B1
(45) Date of Patent: Jan. 10, 2012

(54) HIGH-EFFICIENCY BIOREACTOR AND METHOD OF USE THEREOF

(76) Inventors: Marcos Gonzalez, Davie, FL (US); Sami Benhamou, Aventura, FL (US)

( * ) Notice: Subject to any disclaimer, the term of this patent is extended or adjusted under 35 U.S.C. 154(b) by 0 days.

(21) Appl. No.: 13/164,007

(22) Filed: Jun. 20, 2011

(51) Int. Cl.
*B01D 61/24* (2006.01)
*B01D 63/02* (2006.01)
*C12P 5/00* (2006.01)
*C12P 7/64* (2006.01)
*B01D 61/00* (2006.01)
*C12P 7/00* (2006.01)

(52) U.S. Cl. ..... 210/649; 210/650; 210/651; 435/257.1; 435/906; 435/134; 435/166

(58) Field of Classification Search .......... None
See application file for complete search history.

(56) References Cited

U.S. PATENT DOCUMENTS

| | | | |
|---|---|---|---|
| 3,856,569 A | 12/1974 | Strong | |
| 4,940,547 A | 7/1990 | Cho et al. | |
| 6,979,308 B1 | 12/2005 | MacDonald et al. | |
| 7,063,788 B2 | 6/2006 | Mahendran et al. | |
| 7,166,223 B2 | 1/2007 | Bomberger et al. | |
| 2009/0181438 A1 | 7/2009 | Sayre | |
| 2009/0203116 A1 | 8/2009 | Bazaire | |
| 2011/0174734 A1* | 7/2011 | Seibert et al. | 210/650 |

* cited by examiner

*Primary Examiner* — Krishnan S Menon
(74) *Attorney, Agent, or Firm* — B. Y. Mathis

(57) ABSTRACT

Methods and systems for growing algae are disclosed. For example, disclosed is an exemplary bioreactor for growing algae that includes a chamber, a liquid-permeable membrane that includes a plurality of hollow fiber membranes disposed within the chamber. Each hollow fiber membrane can include a hollow interior and may be made of a liquid-permeable, algae-impermeable membrane, and each hollow fiber membrane may be disposed within the chamber. The respective interiors of the hollow fiber membranes may at least partially define an inner-capillary space (ICS). The interior of the chamber and respective exteriors of the hollow fiber membranes may at least partially define an extra-capillary space (ECS). When algae is grown in the ECS, lipids produced by the algae may be extracted from the ECS to the ICS via the hollow fiber membranes without killing the majority of algae and while containing the algae to the ECS.

11 Claims, 6 Drawing Sheets

HIGH-EFFICIENCY BIOREACTOR AND METHOD OF USE THEREOF

BACKGROUND

I. Field

This disclosure relates to methods and systems usable to grow algae and harvest algae byproducts.

II. Background

Generally, it is known that plants may be used to produce a number of fuels and edible products. This concept extends to various forms of algae, which have been grown and harvested to produce both animal feed and bio-diesel fuels. Unfortunately, such algae-based technologies are not matured to the point where bio-diesel may be produced at a marketable price. Accordingly, new technologies relating to growing algae and harvesting their by-products may be desirable.

SUMMARY

Various aspects and embodiments of the invention are described in further detail below.

In an embodiment, a bioreactor for growing algae includes a chamber, a liquid-permeable membrane that includes a plurality of hollow fiber membranes disposed within the chamber, each hollow fiber membrane including a hollow interior and made of a liquid-permeable, algae-impermeable membrane, wherein each hollow fiber membrane is disposed within the chamber, and wherein the respective interiors of the hollow fiber membranes at least partially define an inner-capillary space (ICS), and the interior of the chamber and the respective exteriors of the hollow fiber membranes at least partially define an extra-capillary space (ECS). When algae is grown in the ECS, lipids produced by the algae can be extracted from the ECS to the ICS via the hollow fiber membranes without killing the majority of algae and while containing the algae to the ECS.

In still yet another embodiment, a method for growing algae in a bioreactor having an extra capillary space (ECS) and an inner capillary space (ICS) separated by a liquid-permeable membrane is disclosed. The liquid-permeable membrane may be at least partially composed of a plurality of hollow fiber membranes with each hollow-fiber membrane including a hollow interior and being made of a liquid-permeable, algae-impermeable material. The respective interiors of the hollow fiber membranes at least partially define the ICS, and the interior of a chamber and the respective exteriors of the hollow fiber membranes at least partially define the ECS. The method includes growing algae in the ECS, extracting lipids from the algae, and transferring the lipids from the ECS to the ICS through the liquid-permeable membrane while containing the algae to the ECS and without killing the majority of the algae.

BRIEF DESCRIPTION OF THE DRAWINGS

The features and nature of the present disclosure will become more apparent from the detailed description set forth below when taken in conjunction with the accompanying drawings in which reference characters identify corresponding items.

DETAILED DESCRIPTION

The disclosed methods and systems below may be described generally, as well as in terms of specific examples and/or specific embodiments. For instances where references are made to detailed examples and/or embodiments, it should be appreciated that any of the underlying principals described are not to be limited to a single embodiment, but may be expanded for use with any of the other methods and systems described herein as will be understood by one of ordinary skill in the art unless otherwise stated specifically.

Figure 1:
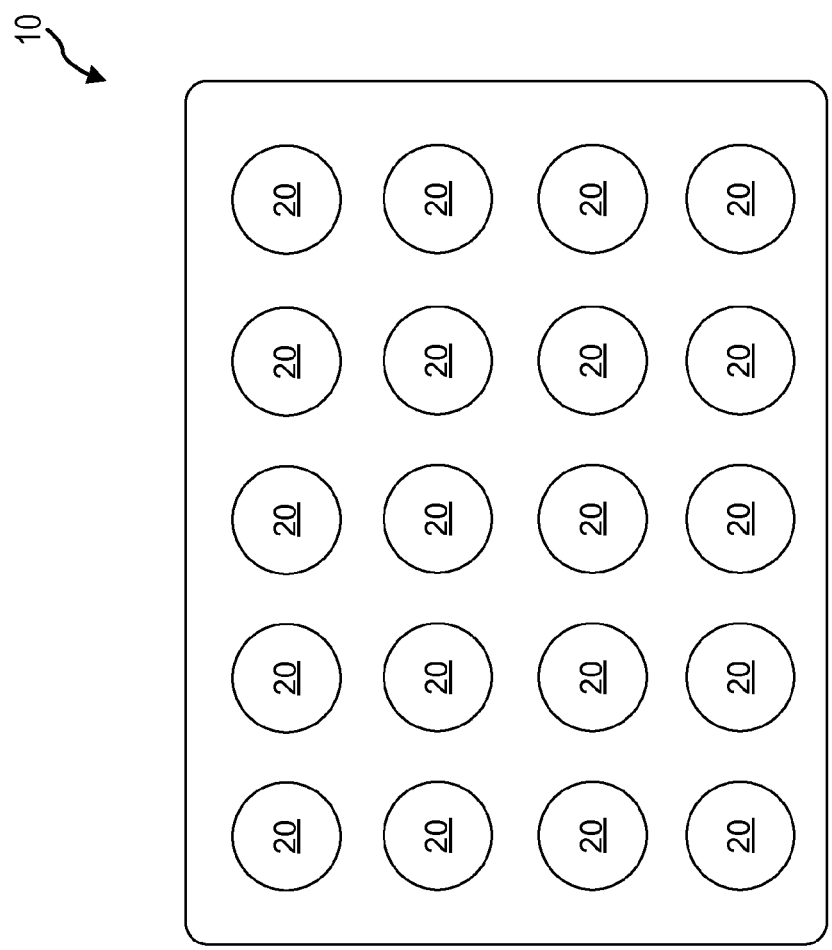
FIG. 1 is a top-down view of an array of exemplary bio-reactors.

FIG. 1 is a top-down view of an exemplary array 10 of bio-reactors 20. As shown in FIG. 1, the array 10 is composed of twenty bio-reactors 20 arranged in a 5-by-4 square matrix. However, it is to be appreciated that the number and particular distribution of the individual bio-reactors 20 may change from embodiment to embodiment.

Figure 2:
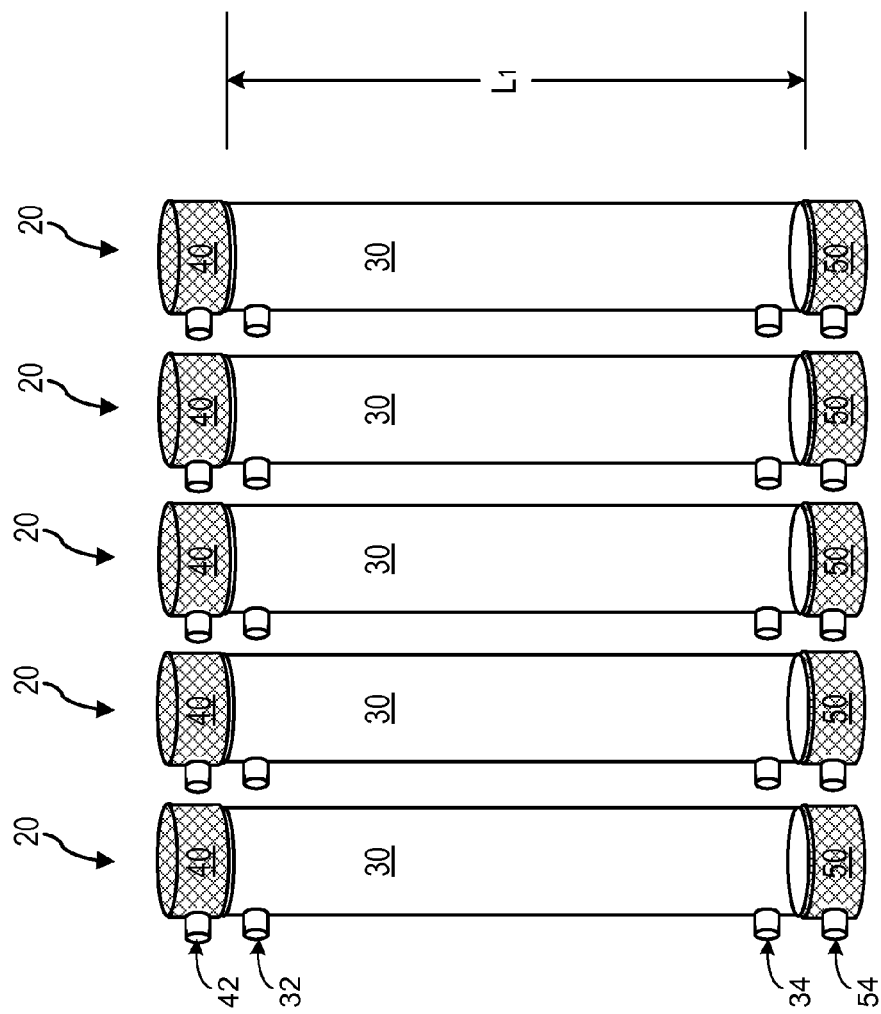
FIG. 2 depicts a side-view of a row of the exemplary bio-reactors of FIG. 1.

FIG. 2 depicts a side-view of a row of the exemplary bio-reactors 20 of FIG. 1. As shown in FIG. 2, each bio-reactor 20 includes a chamber, which in the present example may be a vertically-disposed cylindrical tube 30 (having length $L_1$) coupled to an upper manifold 40 and a lower manifold 50. The cylindrical tube 30 includes an intake port 32 and an outlet port 34. The upper manifold 40 includes an intake port 42 while the lower manifold 50 includes an outlet port 54. In various embodiments, the cylindrical tube 30, upper manifold 40, and lower manifold optionally may be made of transparent or translucent material so as to allow sunlight and/or artificial light to enter the cylindrical tube 30.

While it may not be necessary for the bio-reactors 20 to be vertically oriented in order to grow algae, it is to be appreciated that the vertical orientation may allow for far more efficient land use, thus allowing algae to grow along the entire length $L_1$ of tubes 30—assuming that there is appropriate sunlight and/or artificial light exposure along length $L_1$.

Figure 3:
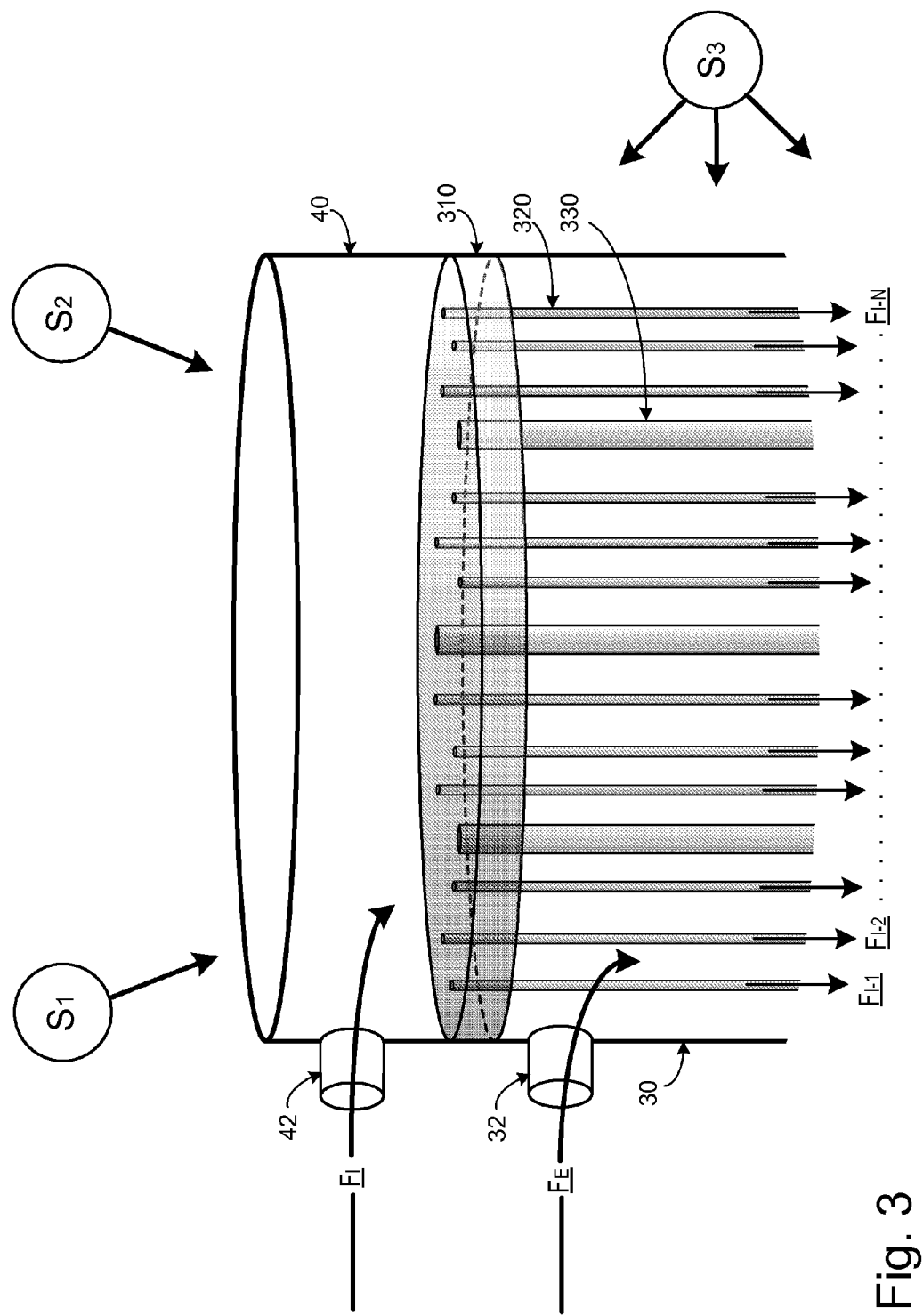
FIG. 3 shows details of the top of an exemplary bio-reactor.

FIG. 3 shows details of the top of an exemplary bio-reactor 20 of FIG. 2 including a portion of the cylindrical tube 30 and the upper manifold 40. As shown in FIG. 3, the exemplary tube 30 may contain a number of hollow fiber membranes 320 and optional light-pipes 330, i.e., the hollow fiber membranes 320 and optional light-pipes 330 may be disposed in tube 30. The hollow fiber membranes 320 and light-pipes 330 may be positioned using a disc 310 according to a predetermined distribution.

In the exemplary embodiment, the disc 310 can be made from a potable polymer and may be made to be transparent or translucent. However, the makeup and light-related properties of the disc 310 may change from embodiment to embodiment without departing from the spirit and scope of the present disclosure.

In operation, a first water flow F, may be established by forcing water into manifold 40 via inlet 42. The water (or other fluid) flow $F_1$ may be divided/distributed into sub-flows $F_{I\text{-}1} \ldots F_{I\text{-}N}$. Each sub-flow $F_K$ of water/fluid may then flow along length $L_1$ to the lower manifold 50, whereby the various sub-flows $F_{I\text{-}1} \ldots F_{I\text{-}N}$ may be recombined into a single flow. In the present embodiment, the lower manifold 50 may be similarly structured to the upper manifold 40 and contain a disc comparable to disc 310. The recombined flow may then exit via outlet port 54. For the purpose of this disclosure, the combined space within the respective interiors of the various hollow fiber membranes 320, as well as those spaces directly coupled to the inside of such hollow fiber membranes 320 (e.g., the spaces with manifolds 40 and 50), can be referred to as the "inner capillary space" (ICS) of the bio-reactor 20.

A second water/fluid flow $F_E$ may be established by feeding water/fluid into inlet port 32, and extracting such fluid from outlet port 54. Also for the purpose of this disclosure, the space within tube 30, but external to the respective exteriors of the various hollow membranes 320, may be referred to as the "extra capillary space" (ECS) of the bio-reactor 20, and the space within tube 30 but external to various hollow membranes 320 may at least partially define the ECS.

Figure 4:
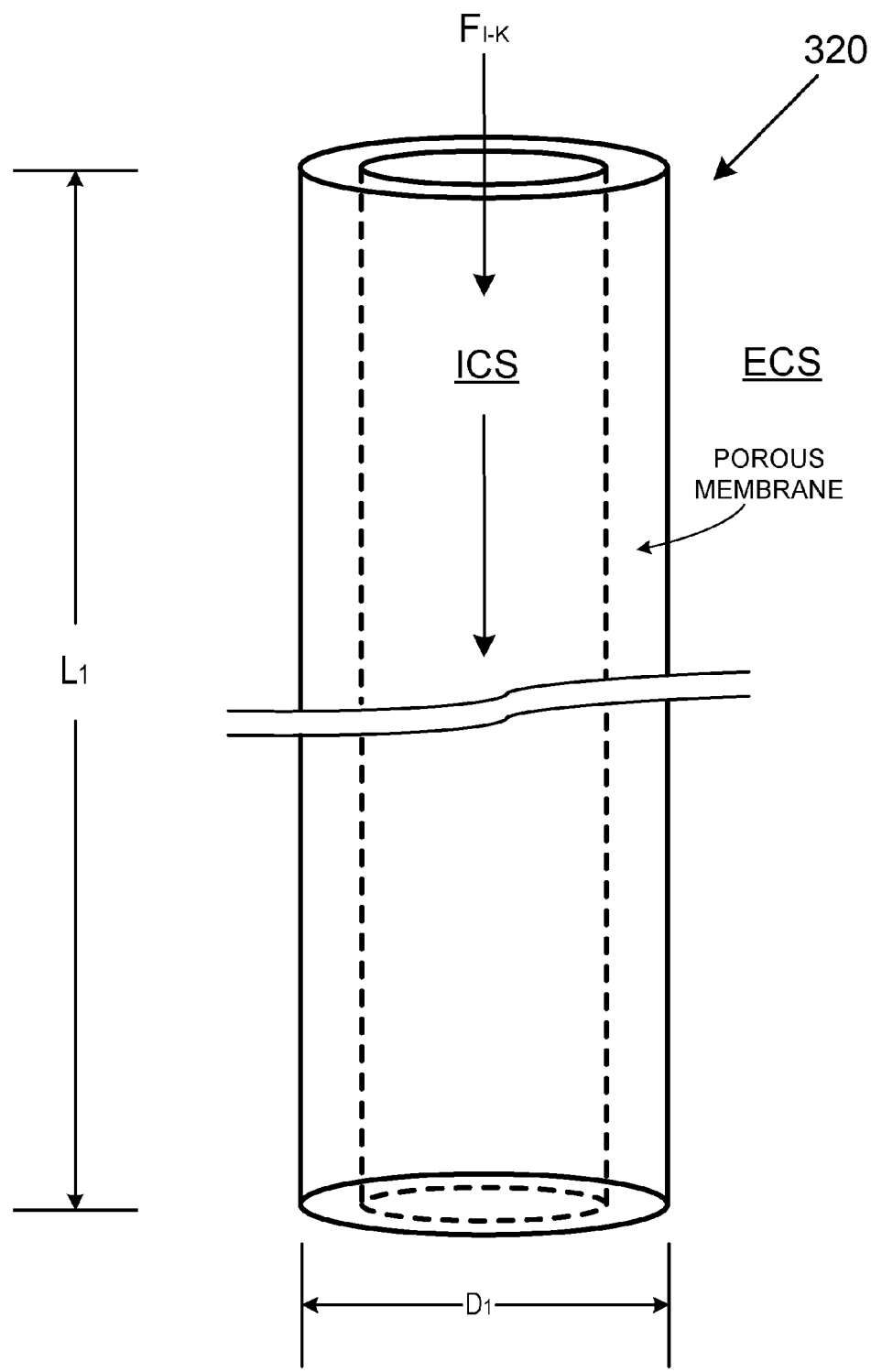
FIG. 4 depicts an exemplary hollow-fiber membrane usable in the bio-reactor of FIGS. 2-3.

Referring to FIG. 4, an individual exemplary hollow fiber membrane 320 is depicted with reference to the ECS, ICS and fluid flow $F_{I-K}$ along the ICS. It is to be appreciated that the exemplary hollow membrane 320 may be porous in nature so as to be fluid-permeable, i.e., it may be constructed so that fluids may pass between the ECS and ICS whenever certain forces, such as osmotic or physical pressure, are applied. It is also to be appreciated that the diameter $D_1$ of the exemplary hollow membrane 320 may vary from embodiment to embodiment as a function of inter alia a particular algae species, which can be cultured/grown in the ECS so that individual algae specimens adhere to the outside of membrane 320. It is also to be appreciated that the size of individual pours of the exemplary hollow membrane 320 (not shown in FIG. 4) may vary so as to make the hollow fiber membrane 320 impermeable to the particular algae species used while still being permeable to liquids. Note that the interior of each hollow fiber membrane 320 partially defines the ICS along with the connected space of the manifolds (40, 50).

The available outer surface area of each membrane 320 may be defined as $(\pi \times D_1 \times L_1)/2$, and thus it should be appreciated that the amount of surface area available for algae growth in the exemplary bio-reactor 20 may be made orders of magnitude greater than the surface area available of conventional bio-reactors, especially in light of the relatively low square-footage needed for the exemplary bio-reactor 20. For example, assuming a bio-reactor having a tube with a vertical length of seven meters has a diameter of one meter, and contains five-hundred membranes 320 with each membrane 320 having an external diameter of 2 millimeters, the available surface area available for algae growth may be calculated as $500(\pi \times 0.002 \times 7)/2 = 11$ square meters not including the surface area of the tube/chamber 30, which accounts for another $(\pi \times 1 \times 7)/2 = 11$ square meters of growth area.

Referring back to FIG. 3, it should also be appreciated that the number and distribution of the tubular membranes 320 and light-pipes 330 may vary from embodiment to embodiment. However, it is also to be appreciated that such distributions may be optimized according to a number of criteria, such as optimizing light distribution within tube 30. Generally, the light pipes 330 may be used to collect light from light sources, such as the sun (S1) and man-made lamps (S2), and re-distribute the collected light within tube 30. Accordingly, light may be made available to the inside of tube 30 internally as well as externally.

While the exemplary light-pipes 330 may be passive elements, it should be appreciated that the light-pipes 330 may be supplemented or replaced with active elements. For example, each light-pipe 330 may be constructed to contain a fluorescing mixture of gases that will emit light when electrically excited.

Note that as individual membranes 320 may also be configured to conduct light similarly to dedicated light-pipes 330, it may be possible to remove light pipes 330 from consideration in various embodiments.

Figure 5:
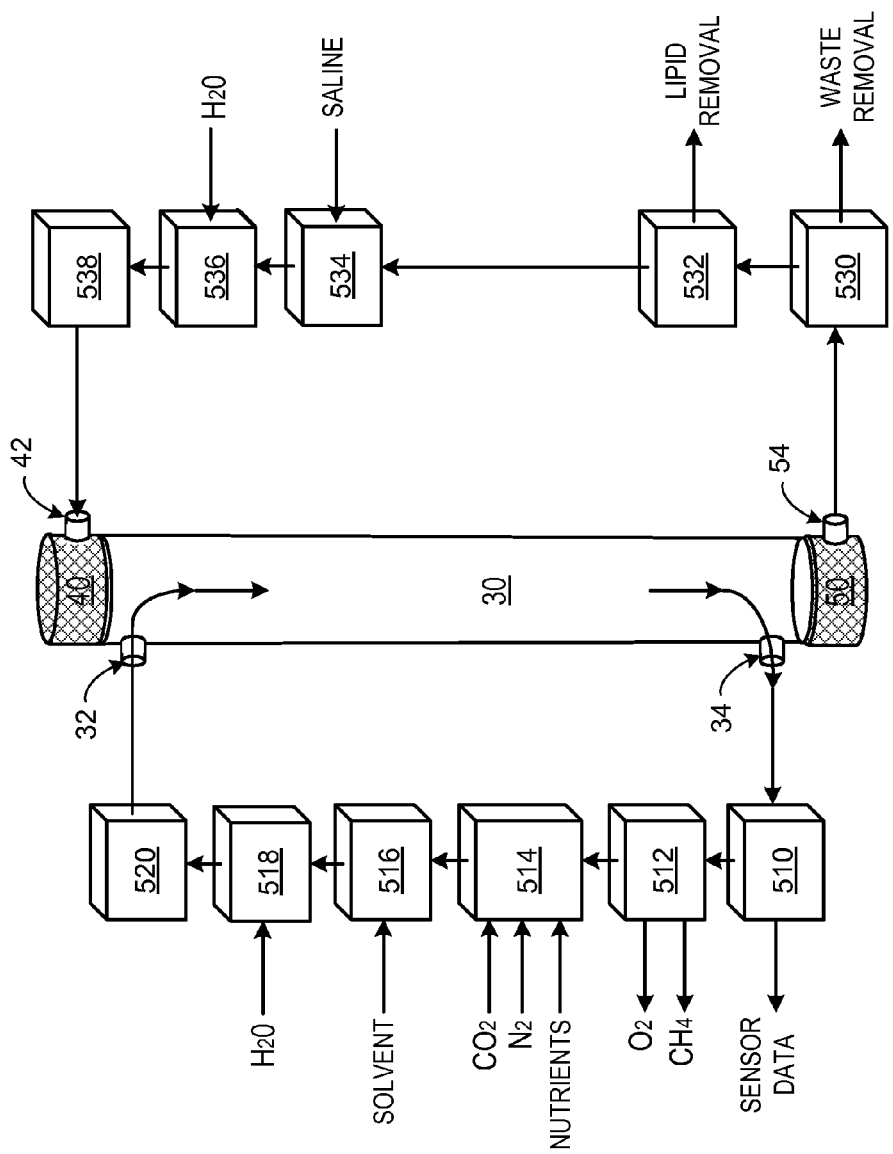
FIG. 5 shows the bio-reactor of FIGS. 2-3 in concert with a first set of devices usable to service the extra-capillary space of the bio-reactor, and a second set of devices usable to service the inner-capillary space of the bio-reactor.

FIG. 5 shows the bio-reactor 20 of FIGS. 2-3 in concert with a first set of devices 510-550 usable to service the ECS of the bio-reactor 20, as well as a second set of devices 530-538 usable to service the ICS of the bio-reactor 20.

The first set of exemplary devices 510-520 include a sensor system 510, a gas extraction device 512, a gas and nutrient infusion device 514, a solvent infusion device 516, a water infusion device 518 and a pumping device 520.

In operation, the ECS space of tube 30 may be filled with water supplied by the water-infusion device 518 and made to flow from the inlet port 32 to the outlet port 34 by virtue of the pumping device 560. One or more algae species may be introduced into the tube 30.

As is known in the relevant arts, biological organisms such as algae may benefit from a combination of nutrients and gases, e.g., carbon dioxide, nitrogen and fertilizer. Accordingly, the gas and nutrient infusion device 514 may be used to feed and promote the growth of such algae by adding an appropriate combination of gases and nutrients to the ECS environment. Similarly, as such organisms are known to produce gases, such as oxygen and methane, the gas extraction device 51 may be used to extract such gases from the ECS environment. Also, as algae are known to produce waste-products that may be toxic to the algae when such waste-products are too concentrated, the sensor device 510 may be used to monitor such waste. Accordingly, by virtue of devices 510-520 the ECS environment of tube 30 may be used to produce and maintain a medium highly conducing to algae growth.

The second set of exemplary devices 530-538 includes a waste removal device 530, a lipid removal device 532, a saline control device 534, a water infusion device 536 and a pumping device 538.

In operation, the ICS of tube 30 may be filled with water supplied by the water-infusion device 536 and made to flow from the inlet port 42 to the outlet port 54 by virtue of the pumping device 538.

It is to be appreciated that as algae in the ECS is multiplying and engorging with lipids, waste produced by algae may be removed from the ECS using the ICS whenever the sensor data of device 510 indicates a condition that the ECS contains too much waste. In such a condition, waste may be removed by forcing the water in the ICS to be more saline than the water of the ECS by use of the saline control device 534, i.e., osmotic pressure can be used. Alternatively, a pressure differential between the ECS and ICS may be created using devices 536 and/or 538 to force waste removal, i.e., trans-membrane pressure (TMP) may be applied.

A particular advantage of the exemplary bio-reactor 20 is that lipids can be removed from algae without the need to harvest/kill the algae. Subsequent to lipid removal the depleted (but living) algae may then be allowed to re-engorge themselves with lipids with the appropriate conditions. For example, assume that algae growth has reach a maximum (or near so) potential in the ECS with the algae being generally engorged with lipids. By applying a solvent via the solvent infusion device 516, lipids may be expunged from the algae into the liquid medium of the ECS. By then applying TMP (or alternatively osmotic pressure), the lipids may be forced from the ECS into the ICS, and then extracted by the lipid removal device 532. Thus, a beneficial substance produced by algae may be harvested without killing the algae and while containing the algae to the ECS.

After the lipids are removed from the bio-reactor 20, the algae may then begin another feeding cycle so that they may again become engorged with lipids. Upon such engorgement (encouraged by light and the appropriate gases and nutrition), the above-described lipid removal cycle may be repeated—at least until the algae become physically incapable of repeating such an engorgement-and-removal cycle. At such time, the algae may be removed from the ECS and appropriately processed to remove further lipids, and also to be processed for other substances that may be used in other industries, e.g., in the cosmetics industry, to produce butinole, to create animal nutrition supplements, and so on.

Figure 6:
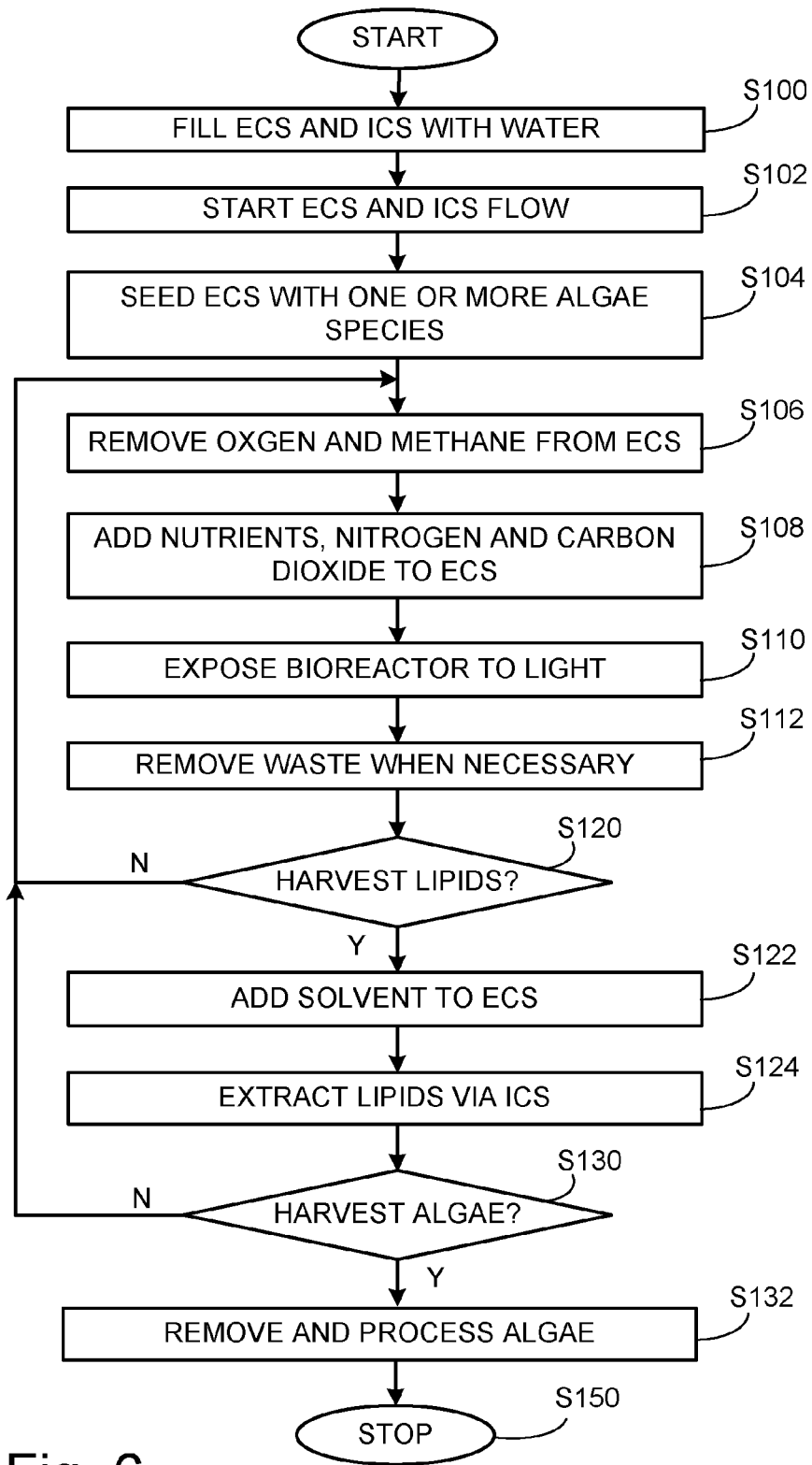
FIG. 6 is a flowchart outlining a first exemplary operation of the disclosed methods and systems.

FIG. 6 is a flowchart outlining a first exemplary operation of the disclosed methods and systems for growing and harvesting algae and algae by-products. While the below-described steps are described as occurring in a particular sequence for convenience, it is to be appreciated by those skilled in the art that the order of various steps may be changed. It is further to be appreciated that various steps may occur simultaneously or be made to occur in an overlapping fasion.

The operation starts in step S100 where the ECS and ICS of a bio-reactor are filled with water. Next, in step S102 water/fluid flow in the ECS and ICS may be established. Then, in step S104 the ECS may be seeded with one or more algae species. Control continues to step S106.

In step S106, oxygen and methane produced by the algae can be removed from the ECS. Next, in step S108 nutrients and beneficial gases, e.g., carbon dioxide and nitrogen can be infused into the fluid of the ECS. Then, in step S110 the ECS can be exposed to light (e.g., sunlight and/or man-made light, e.g., using the light-pipes 330 of FIG. 3) to the extent possible or practical. Thus, by virtue of steps S106-S110, which may be made to occur simultaneously or in an overlapping fashion, algae within the ECS may engorge themselves, multiply, and adhere themselves to the available surface areas of the ECS. Control continues to step S112.

In step S112, waste may be removed from the ECS if necessary. As discussed above, such waste removal may be accomplished by applying osmotic pressure or TMP between a respective ECS and ICS (assuming an appropriate liquid-permeable, alga-impermeable membrane separates the ECS and ICS) to allow waste to flow from the ECS to the ICS. Thereafter an appropriate device or process may be used to remove the waste from the ICS noting that waste removal may occur while algae is multiplying and/or becoming engorged with lipids. Next, in step S120 a determination may be made as to whether it may be desirable to harvest lipids from the algae of the ECS. If a lipid harvest is desirable, control continues to step S122; otherwise, control jumps back to step 106.

In step S122 a solvent (or other appropriate substance) may be added to the ECS in order to expunge lipids from the algae into the fluid medium of the ECS. Next, in step S124, while containing the algae to the ECS (and without killing the majority of the algae), the lipids may be extracted from the ECS into the ICS using osmotic pressure or TMP across an appropriate liquid-permeable, algae impermeable membrane, such as the membranes of the above-described hollow fiber membranes. Control continues to step S130.

In step S130, a determination may be made as to whether it may be desirable to harvest the algae of the ECS, e.g., it appears that the algae crop within the ECS is not sufficiently viable so as to effectively/economically perform another lipid engorgement/removal cycle. If algae harvest is desirable, control continues to step S132; otherwise, control jumps back to step 106. Note that the number of cycles for lipid harvest and removal may vary from embodiment to embodiment and using different types of algae. Accordingly, in a first embodiment with a first algae only two engorgement/harvest cycles may be performed while in a second more cycles may be plausible.

In step S132, the algae may be physically removed from the bio-reactor and appropriately processed for more lipids and other beneficial substances. Control continues to step S150 whereby the process stops noting that the process may be optionally repeated starting at step S100.

What has been described above includes examples of one or more embodiments. It is, of course, not possible to describe every conceivable combination of components or methodologies for purposes of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method for growing algae in a bioreactor having an extra capillary space (ECS) and an inner capillary space (ICS) separated by a liquid-permeable membrane, the liquid-permeable membrane comprising a plurality of hollow fiber membranes with each hollow-fiber membrane including a hollow interior and being made of a liquid-permeable, algae-impermeable material, wherein the respective interiors of the hollow fiber membranes at least partially define the ICS, and the interior of a chamber and respective exteriors of the hollow fiber membranes at least partially define the ECS, the method comprising:
growing algae in the ECS;
extracting lipids from the algae; and
transferring the lipids from the ECS to the ICS through the liquid-permeable membrane while containing the algae to the ECS and without killing the majority of the algae,
wherein individual algae specimens are cultured on the outside surface of the hollow fiber membranes.

2. The method of claim 1, wherein the bioreactor includes a first manifold and a second manifold connected to the ICS in such a way as to allow fluids to flow from the first manifold to the second manifold via the respective interior spaces of the hollow fiber membranes to allow removal of the lipids from the bioreactor.

3. The method of claim 2, wherein step of transferring the lipids from the ECS to the ICS uses mechanical pressure across the liquid-permeable membrane.

4. The method of claim 2, wherein the bioreactor includes a vertically disposed tube, and the first and second manifolds are attached at the ends of the tube.

5. The method of claim 2, wherein the step of extracting lipids from the algae includes exposing algae in the ECS to a solvent, and during such exposure time lipids are extracted from the algae and absorbed into the ICS via the liquid-permeable membrane.

6. The method of claim 5, further comprising exposing the algae to gases and nutrients to thus re-engorge the algae with lipids.

7. The method of claim 5, further comprising removing algae waste from the ECS to the ICS via the liquid-permeable membrane during periods when the algae is multiplying and/or engorging with lipids.

8. The method of claim 7, wherein the step of removing waste from the ECS to the ICS uses mechanical pressure across the liquid-permeable membrane.

9. The method of claim 6, further comprising repeating the steps of re-engorgement and lipid removal at least two additional times.

10. The method of claim 9, further comprising harvesting the algae after repeating the steps of re-engorgement and lipid removal.

11. The method of claim 1, further comprising providing light to algae using one or more light-pipes located within the bioreactor.

\* \* \* \* \*